(12) United States Patent
Olivier et al.

(10) Patent No.: US 7,435,339 B2
(45) Date of Patent: Oct. 14, 2008

(54) FILTER DEVICE INTEGRATING SAMPLED VOLUME CONTROL

(75) Inventors: Stéphane Olivier, Rosheim (FR);
Jérôme Geyer, Wahlenheim (FR);
Bertrand Engel, Dimbsthal (FR);
Christian Clauss, Obernai (FR)

(73) Assignee: Millipore Corporation, Billerica, MA (US)

( * ) Notice: Subject to any disclaimer, the term of this patent is extended or adjusted under 35 U.S.C. 154(b) by 516 days.

(21) Appl. No.: 10/525,492

(22) PCT Filed: Oct. 24, 2003

(86) PCT No.: PCT/IB03/05116

§ 371 (c)(1),
(2), (4) Date: Feb. 23, 2005

(87) PCT Pub. No.: WO2004/037385

PCT Pub. Date: May 6, 2004

(65) Prior Publication Data

US 2006/0163125 A1    Jul. 27, 2006

(30) Foreign Application Priority Data

Oct. 28, 2002    (FR) .................................. 02 13482

(51) Int. Cl.
*B01D 17/12* (2006.01)
(52) U.S. Cl. .................... 210/86; 73/863.01; 73/863.23; 73/864.34; 210/143; 210/321.6; 210/416.1; 422/101; 422/105
(58) Field of Classification Search ............ 210/85, 210/86, 97, 109, 134, 143, 321.6, 416.1; 73/863.01, 863.02, 863.23, 864.34, 864.73; 422/101, 119, 103–110; 177/1, 2, 4, 25.11, 177/25.12, 25.14, 60; 700/267, 273
See application file for complete search history.

(56) References Cited

U.S. PATENT DOCUMENTS 4,678,576 A    7/1987    Leoncavalo (Continued)

FOREIGN PATENT DOCUMENTS

WO    WO 01/48141 A1    7/2001

(Continued)

OTHER PUBLICATIONS

International Search Report dated Feb. 27, 2004.

*Primary Examiner*—Joseph W Drodge (57) ABSTRACT

The invention relates to a drainage device for a filter unit for microbiological testing of liquids, said drainage device including a mechanical support (10), which is adapted to receive a filter unit (16), and an suction pump (22) connected to said mechanical support to aspirate a liquid substance contained in said filter unit. The device comprises: a weight sensor (18) on which said mechanical support is mounted; a user interface (26) for entering data relating to drainage and/or said liquid substance; and a control unit (24) connected to said suction pump (22), the weight sensor (18) and said user interface (26), said control unit (24) being adapted to determine, from said data, at least a first weight corresponding to a first representative signal; and, when said weight sensor (18) supplies a signal corresponding to said first signal, said control unit (24) starts operation of said suction pump (22) so as to aspirate said liquid substance contained in said filter unit (16).

13 Claims, 10 Drawing Sheets

U.S. PATENT DOCUMENTS

| | | | |
|---|---|---|---|
| 5,092,988 A * | 3/1992 | Womack et al. | 210/85 |
| 5,096,588 A * | 3/1992 | Albertson | 210/617 |
| 5,172,332 A * | 12/1992 | Hungerford et al. | 700/267 |
| 5,234,585 A | 8/1993 | Zuk | |
| 5,306,420 A | 4/1994 | Bisconte | |
| 6,027,638 A | 2/2000 | Johnson | |
| 6,133,045 A | 10/2000 | Johnson et al. | |
| 6,171,480 B1 * | 1/2001 | Lee et al. | 210/85 |
| 6,358,730 B1 | 3/2002 | Kane | |
| 6,884,341 B2 | 4/2005 | Ferguson | |
| 6,905,594 B2 | 6/2005 | Ferguson | |
| 7,067,055 B2 * | 6/2006 | Ruppel | 210/85 |
| 2004/0000518 A1 * | 1/2004 | Haley, III | 210/615 |
| 2005/0233436 A1 | 10/2005 | Clauss | |

FOREIGN PATENT DOCUMENTS

| | | |
|---|---|---|
| WO | WO 02/068580 A2 | 9/2002 |

* cited by examiner

FILTER DEVICE INTEGRATING SAMPLED VOLUME CONTROL

CROSS REFERENCE TO RELATED APPLICATIONS

This application is the U.S. National Stage Application of International Application No.: PCT/2003/IB2003/005116, filed on Oct. 24, 2003, which claims priority to French Application No.: 0213482, filed Oct. 28, 2002.

The present invention relates to a device for draining a filter unit for microbiological testing of liquid substances.

Said filter unit includes a membrane on which the microorganisms contained in the liquid substance are concentrated. The membrane is then placed in an agar culture medium to encourage the growth of said microorganisms.

There are prior art drainage devices adapted to force a sample of a liquid substance to be analyzed through a membrane by creating a reduced pressure on the downstream side of the membrane, whilst avoiding contamination of said sample.

These devices generally include a vacuum pump connected to a flask to create a reduced pressure therein, said drainage device, consisting of a receptacle closed at the bottom by said membrane, being mounted directly on the flask. Thanks to the suction induced by the reduced pressure, the sample of liquid substance contained in said receptacle is aspirated into the flask and the microorganisms are retained by the membrane.

An installation of the above kind has a number of drawbacks and in particular that of its bulk, since it requires a vacuum pump and a large number of pipes.

Furthermore, the flask in which the liquid substance is collected must be drained regularly, which makes it necessary to monitor the level and, on each draining, to re-establish the vacuum inside said flask after the filter unit has been mounted on it. This operation increases the overall time to filter a sample and reduces productivity, in particular when liquid substance samples are analyzed in series.

Moreover, to avoid any contamination of a sample by the installation, it is necessary regularly to sterilize all of the installation in an autoclave.

Consideration has been given to replacing the vacuum pump by a pump adapted to pump the liquid substance directly, but this improvement has not significantly reduced the bulk of the installation and still necessitates a flask.

Moreover, the quantity of liquid substance filtered must be known accurately to determine, after numeration, the concentration in microorganisms of said liquid substance.

The quantity of liquid substance is generally controlled by adjusting the level of said liquid substance relative to a gauge mark on a graduated scale on the surface of the wall of said filter unit.

A problem that arises, and that the present invention seeks to solve, is that of providing a drainage device for a filter unit that not only provides more precise control over the quantity of liquid substance filtered, but also filters liquid substance samples at a high throughput.

To this end, the present invention proposes a drainage device including a mechanical support, which is adapted to receive a filter unit including a membrane, and a suction pump connected to said mechanical support to aspirate a liquid substance contained in said filter unit, which drainage device is characterized in that it comprises:

a weight sensor on which said mechanical support is mounted and which is adapted to deliver a signal representative of the weight exerted by said mechanical support on said weight sensor;

a user interface for entering data relating to the drainage of said filter unit and/or to said liquid substance; and a control unit connected to said suction pump, the weight sensor and said user interface, said control unit being adapted to determine, from said data, at least a first weight corresponding to a first representative signal; and, when said weight sensor supplies a signal corresponding to said first signal, said control unit starts operation of said suction pump so as to aspirate said liquid substance contained in said filter unit.

Thus an advantageous feature of the invention consists in the combination of a mechanical support mounted on a weight sensor, said mechanical support being adapted to receive the filter unit containing said liquid substance, with a control unit and a user interface, the latter enabling entry of data relating to the drainage mode and the quantity of liquid substance to be drained. Said control unit turns on the suction pump as soon as the weight sensor supplies a signal corresponding to the weight of the liquid substance sample to be filtered.

The data relating to the liquid substance, which is entered into a memory of the control unit via the user interface, includes in particular data relating to the volume of liquid substance to be filtered and data relating to the density of the liquid substance. The control unit is then able to calculate the weight of the liquid substance to be filtered and to compare the weight of liquid substance contained in the filter unit to the weight of liquid substance to be filtered. When the weight sensor supplies a signal corresponding to said first signal, the control unit starts the suction pump, the weight of the liquid substance introduced into said filter unit then corresponding to the weight of the liquid to be filtered.

The filter unit can be filled with the liquid substance to be filtered either manually or by means of a filler pump.

Accordingly, thanks to the weight sensor, and using the density, the exact volume of liquid substance to be filtered can be determined, and filtration is effected automatically by the control means, which enables operation of the suction pump as soon as the weight of volume to be filtered is contained in said filter unit.

This allows accurate control of the weight of liquid substance filtered and improves the filtration throughput.

In one particularly advantageous embodiment of the invention, said control unit stops operation of said suction pump when said weight sensor supplies a stationary signal representative of a constant weight exerted on said weight sensor by said mechanical support after said liquid substance has been aspirated.

As a result, during filtration by suction, the weight sensor supplies signals representative of a weight that decreases as a function of time. When the total quantity of liquid substance originally contained in the filter unit has been aspirated, the weight sensor supplies a stationary signal representative of a constant weight, as no further liquid substance is withdrawn from the filter unit. When said weight sensor supplies this stationary signal, said control unit stops the suction pump automatically, which further improves the throughput.

In one particularly advantageous embodiment of the invention, said control unit determines from said data at least a second weight corresponding to a second representative signal and said control unit is adapted to command warning means to warn the user when said weight sensor supplies a signal corresponding to said second signal.

This embodiment of the drainage device can filter a mixture of at least two liquids, said mixture being produced in the filter unit itself.

Thus the volume and density data entered via the user interface and relating to a second liquid substance enable the control unit to operate warning means advising the user to stop pouring the second liquid substance into said filter unit, thanks to the weight sensor, which supplies a second signal representative of the weight of the second liquid substance to be introduced into the filter unit.

The warning means can comprise an indicator of the volume of liquid substance introduced into said filter unit and/or an audible or luminous warning device indicating that said volume has been reached. Clearly, the control unit obtains the volume of the substance by dividing the weight by the density.

Obviously, after the second liquid has been introduced into the filter unit, the drainage device is adapted so that a particular volume of first liquid substance can be introduced and the control unit can operate the suction pump to filter the combination of the two liquid substances.

Said control unit preferably starts the operation of said suction pump after said weight sensor has supplied a stationary signal representative of said first weight.

Thus filtering of the liquid substance really starts only when filling of said filter unit has stopped. A stationary signal from the weight sensor indicates that the first weight is constant and thus that filtration can start.

In a particularly advantageous embodiment of the invention, said mechanical support comprises a reception head for receiving said filter unit, said reception head having a reception surface opposite which said membrane can be disposed and onto which a suction duct discharges, and said reception head includes a passage, one end of which discharges externally of said reception surface and the other end of which discharges onto said reception surface, said reception head comprising a selectively operable valve mobile between a first position in which it shuts off said passage and a second position in which it frees said passage.

Thus the filter unit bears in a sealed manner on the reception surface and the membrane is disposed facing said reception surface. Thus the membrane and the reception surface form two opposite walls of a suction chamber into which discharge the suction duct and a passage that can be vented to the atmosphere. The suction duct that is connected to the suction pump aspirates the liquid substance contained in the filter unit through the membrane.

Thanks to this advantageous feature, the reception head has a passage which connects the reception surface and the exterior of the head to the atmosphere and is shut off by the selectively operable valve during filtering so that no liquid flows through this passage. On the other hand, as soon as all of the liquid substance contained in the filter unit has been aspirated by said suction pump and filtered, the membrane being relatively impermeable to air, it cannot be dried by the small amount of air that is drawn in by the suction pump and passes through it.

The valve is then moved to a second position, to free the passage. Through the passage, the suction pump draws in air from outside the drainage device, which flows into the suction chamber between the membrane and the reception surface, and thence to the suction pump. Thus, thanks to this passage, the membrane is dried with sterile air coming from the environment of said drainage device, which is housed in a hood or near the flame of a Bunsen burner, for example. This allows improved growth of the microorganisms when the membrane is deposited on the nutrient medium, as they do not migrate.

Said control unit advantageously commands movement of said selectively operable valve into said second position and starts the operation of said suction pump when said weight sensor supplies a stationary signal representative of a constant weight exerted on said weight sensor by said mechanical support after said liquid substance has been aspirated.

Accordingly, when the weight sensor supplies a stationary signal representative of a constant weight, this means that the filter unit is empty and that all of the liquid substance has been aspirated by the suction pump. In accordance with this feature, as soon as the weight sensor supplies the stationary signal, the control unit opens the passage for drying the membrane.

Throughput is further improved by this feature, which also initiates drying of the membrane automatically, without human intervention, after the liquid substance has been filtered.

In another particularly advantageous embodiment of the invention, said control unit commands movement of said selectively operable valve into said second position when said weight sensor supplies signals respectively representative of an upper limit weight when said filter unit is placed on said reception head and a lower limit weight when said filter unit is removed from said reception head.

Accordingly, in this embodiment, the membrane is protected from rupturing or deformation.

Because the base of the filter unit and the reception head are frustoconical in shape, for improved centering and to seal the junction between them when the filter unit is fitted to the reception head to form the suction chamber, air trapped between the two tends to apply a stress to the lower surface of the membrane, which can in some circumstances rupture it. This is because the membrane is only very slightly permeable to air, even when it is dry.

By moving the selectively operable valve to the second position when the weight sensor supplies a signal which is representative of an upper limit weight that is much greater than the weight of the liquid substance contained in the filter unit, and of the force exerted to mount the filter unit on the filter head, the passage is opened so that air trapped between the reception head and the filter unit escapes via said passage.

Similarly, when the filter unit is removed from the reception head, a reduced pressure is created in the suction chamber between the membrane and the reception surface of the reception head, and the passage is left open to compensate this reduced pressure. The lower limit weight in fact corresponds to a negative weight, since the weight sensor is entrained in a direction opposite to that of the weight exerted by the liquid substance.

Said control unit preferably commands movement of said selectively operable valve into said second position when said weight sensor supplies a signal whose intensity as a function of time is greater than a predetermined slope, which is much greater than the slope that could be recorded during the operations of filling the filter unit.

According to a further particularly advantageous embodiment of the invention, the drainage unit comprises a frame, said weight sensor extends substantially horizontally between a first end fastened to said frame and a second end that is free with respect to said frame, and said mechanical support rests on said second end of said weight sensor.

Thus the first end of the weight sensor is held in a fixed position on said frame and the mechanical support rests entirely on the second end of the weight sensor so that its deformation, which induces a signal representative of the weight, is related only to the weight of the mechanical support and of the filter unit resting thereon.

Said mechanical support is preferably connected to said suction pump by a tubular member having at least one flexible portion that extends from said mechanical support substantially perpendicularly to the direction of operation of said weight sensor.

Thanks to this feature, the suction pump, which cannot be fastened to the mechanical support, is connected thereto by a tubular member whose flexible portion, which is parallel to the weight sensor, does not interfere with the weight measurement, the tubular member generating a force perpendicular to the direction of operation of said weight sensor.

In another aspect, the present invention provides a drainage device including a mechanical support, which is adapted to receive the filter unit equipped with a membrane, and a suction pump connected to said mechanical support to aspirate a liquid substance contained in said filter unit. Said mechanical support comprises a reception head support entirely fastened to said weight sensor and said reception head is removably fastened to said head support with lockable connecting means.

Thus the reception head can be replaced by another reception head adapted to receive another type of filter unit, for example with a greater volumetric capacity or different kind of filter. Furthermore, thanks to this feature, the reception head is adapted to be sterilized in an autoclave or by immersion in a sterilizing solution, for example, independently of the other components of the drainage device. This prevents contamination of the membrane of a filter unit during a new series of analyses.

In a particularly advantageous embodiment, said head support has a circular cylindrical projecting vertical portion adapted to cooperate with an opening formed in the portion opposite said reception surface of said reception head and said reception head and said projecting vertical portion are fastened together by keying means to form said lockable connecting means.

Thus the various reception heads all have an opening of the same size that is positioned identically in the portion opposite the reception surface so that it can be mounted on the head support, said vertical parts being engaged in said opening.

The head support and the reception head are fastened together by keying means.

The reception head advantageously has a transverse bore adapted to cooperate with a groove formed around said vertical portion and said transverse bore is adapted to receive removable key means.

Accordingly, the transverse bore, which intersects said opening in the reception head, is adapted to receive removable key means, which are mobile in translation in said bore. When the reception head is engaged on said head support, the removable key means are withdrawn from the bore and are afterwards re-inserted to pass through said bore and a portion of the neck of said vertical part. Thus the reception head is secured to said head support against movement in vertical translation.

The head support preferably has a suction branch, one end of which is adapted to be connected to said suction duct of said reception head and the other end of which is adapted to be connected to said suction pump.

The suction head includes the suction duct through which the liquid substance is aspirated and the head support includes a suction branch intended to be connected to said suction duct in order to aspirate the liquid substance via the suction pump. Accordingly, each time the reception head is changed, the suction duct must be connected to the first end of the suction branch in a substantially sealed manner to be able to collect the liquid substance with no leakage of air or liquid substance.

According to an advantageous feature, said head support includes a control device adapted to cooperate with said selectively operable valve to move it into said first position or into said second position.

In this way, the control device is fixedly mounted on the head support and is adapted to operate said selectively operable valve situated in the reception head mechanically. The mechanical means for operating the selectively operable valve to open the passage are explained in more detail later in the description.

Said control device advantageously includes a solenoid whose core is adapted to drive said selectively operable valve.

This device constitutes particularly advantageous means of entraining said valve in a relatively simple way.

The drainage device preferably comprises an armature covered with a casing, bearing on a chassis, said frame is suspended from said armature in the space between said chassis and said armature, and an opening in the casing facing said head support is adapted for mounting and demounting said reception head.

The component parts of the drainage device are explained in more detail in the remainder of the description.

Other features and advantages of the invention will emerge from a reading of the following description of particular embodiments of the invention, provided by way of illustrative but nonlimiting example, which description refers to the appended drawings, in which.

Figure 1:
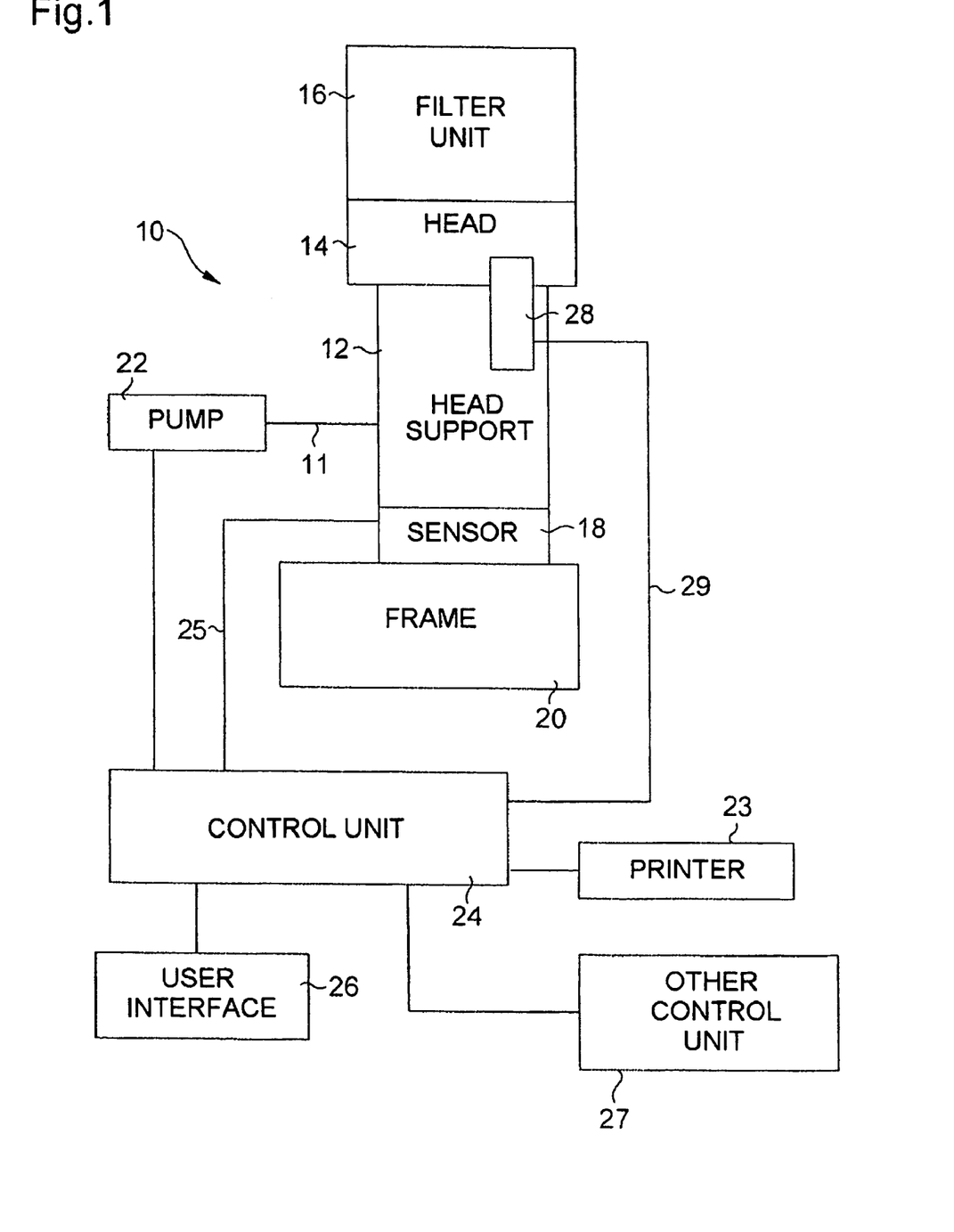
FIG. 1 is a block diagram showing the components of the drainage device according to the invention and the connections between them.

The component parts of the drainage device according to the invention and the functional links between them are described with reference to FIG. 1.

The drainage device includes a mechanical support 10 consisting of a head support 12 and a reception head 14 mounted on the head support 12. The reception head 14 is adapted to receive a filter unit 16 able to contain a liquid substance to be filtered.

The assembly comprising the filter unit 16, the reception head 14, and the head support 12 is mounted on and rests on a weight sensor 18 which is in turn mounted on a frame 20 in a fixed position.

The mechanical support 12 is connected by a tubular member 11 to a suction pump,22 which aspirates the liquid substance contained in said filter unit 16 in a manner described in more detail hereinafter. The suction pump 22 is controlled by a control unit 24 that is connected by an electrical connection 25 to the weight sensor 18 to control said suction pump 22, in particular as a function of information supplied by the weight sensor 18.

The drainage device further includes a user interface 26 connected to the control unit 24, for entering data relating to the liquid substance to be filtered and to the mode of operation, which is a function of the type of filter unit used, and also to display and/or export data. To this end, the control unit 24 is connected to a printer 23 and to another control unit 27, comprising a microcomputer, for example.

The head support 12 further includes a solenoid 28 connected by an electrical connection 29 to the control unit 24 and adapted in particular to control an air inlet situated in the reception head 14 and described in more detail hereinafter.

Figure 2:
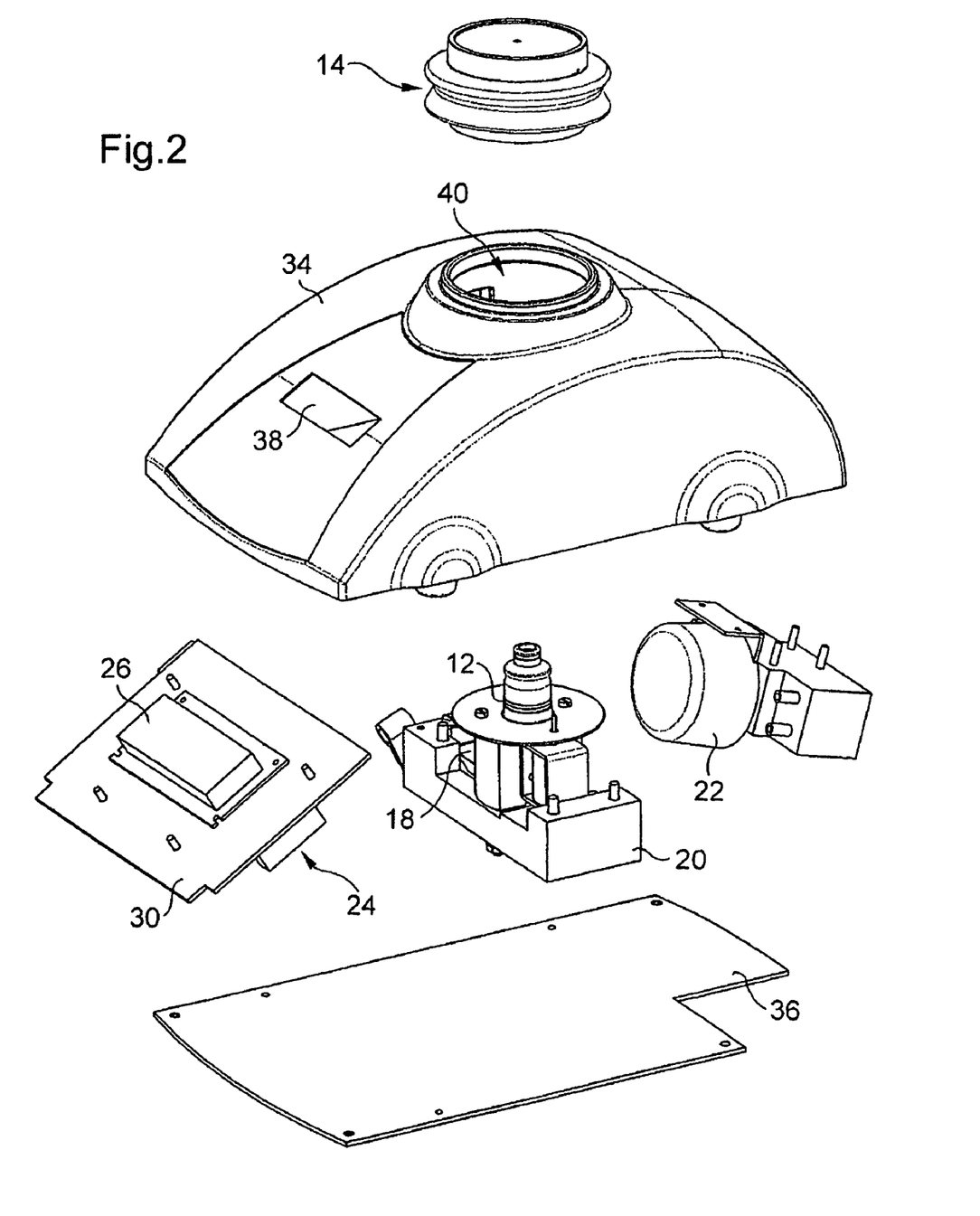
FIG. 2 is a diagrammatic exploded perspective view of the drainage device according to the invention.

FIG. 2 is an exploded view of a portion of the drainage device according to the invention, showing the suction pump 22, the frame 20 on which the weight sensor 18 (shown in more detail in FIG. 4) is mounted, and the head support 12.

The control unit 24 is mounted on the rear surface of a support plate 30, the front face of the support plate 30 comprising the user interface 26 and in particular warning means 32 that include a display screen in particular.

The assembly comprising the frame 20, the suction pump 22, and the control unit 24 is housed in a casing 34 closed at the bottom by a bottom plate 36.

The support plate 30 is mounted inside said casing 34 so that the user interface 26 is on the front portion 38 of the casing 34. The frame 20 is suspended from said casing so that the head support 12 projects from an opening 40 formed in the upper portion of the casing 34. The suction pump 22 is accommodated in the rear portion of the casing 34.

Figure 3:
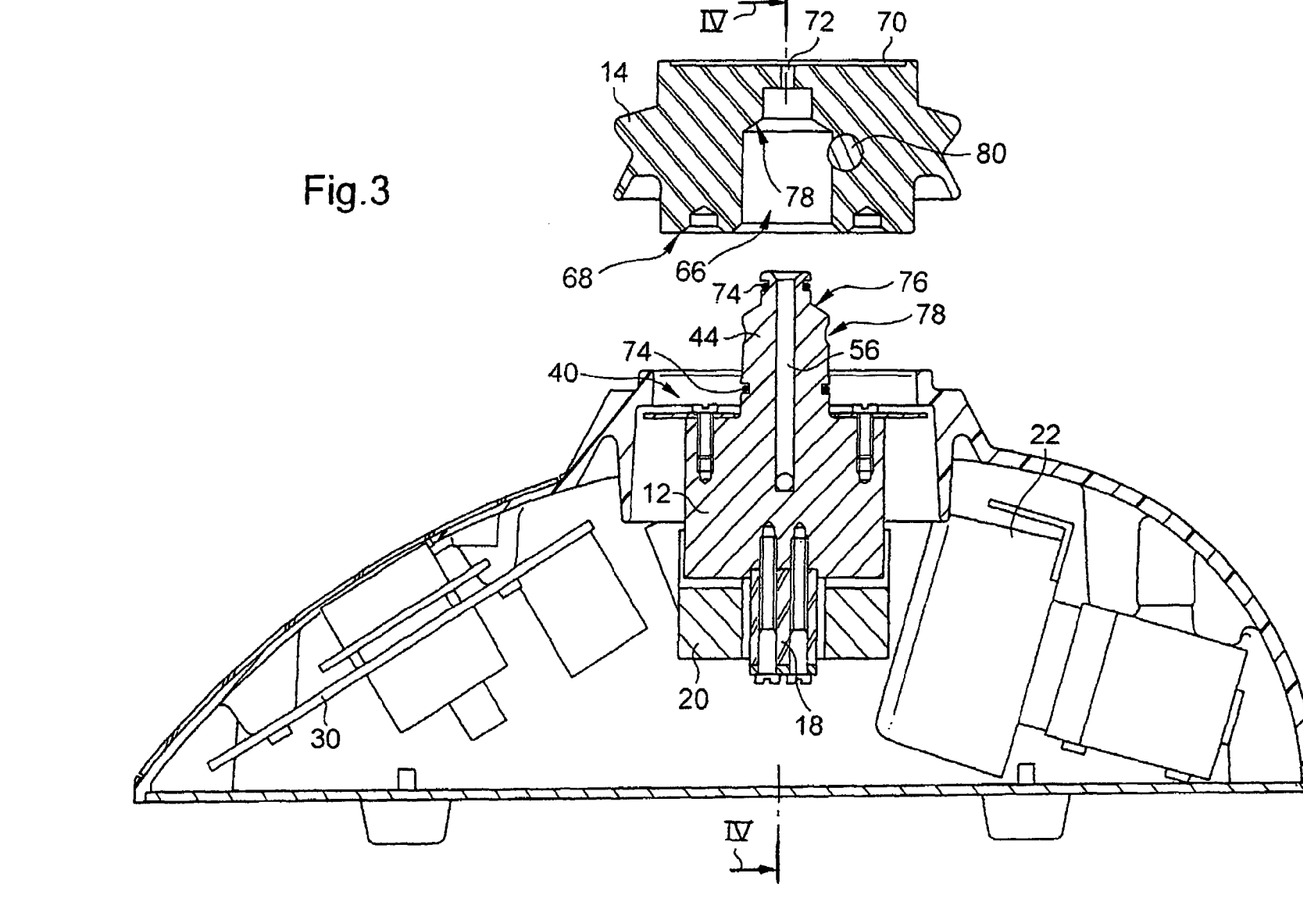
FIG. 3 is a diagrammatic view in longitudinal vertical section of the drainage device.

FIG. 3 is a view in vertical longitudinal section of the casing 34 of the drainage device according to the invention in which are accommodated the suction pump 22, the support plate 30, and the frame 20.

The frame 20 comprises the weight sensor 18, which is shown here in cross section, and the head support 12, which has a projecting vertical portion 44 that passes through the opening 40 in the casing 34.

FIG. 3 also shows the reception head 14 which faces the head support 12, which is described in detail with reference to FIG. 7.

Figure 7:
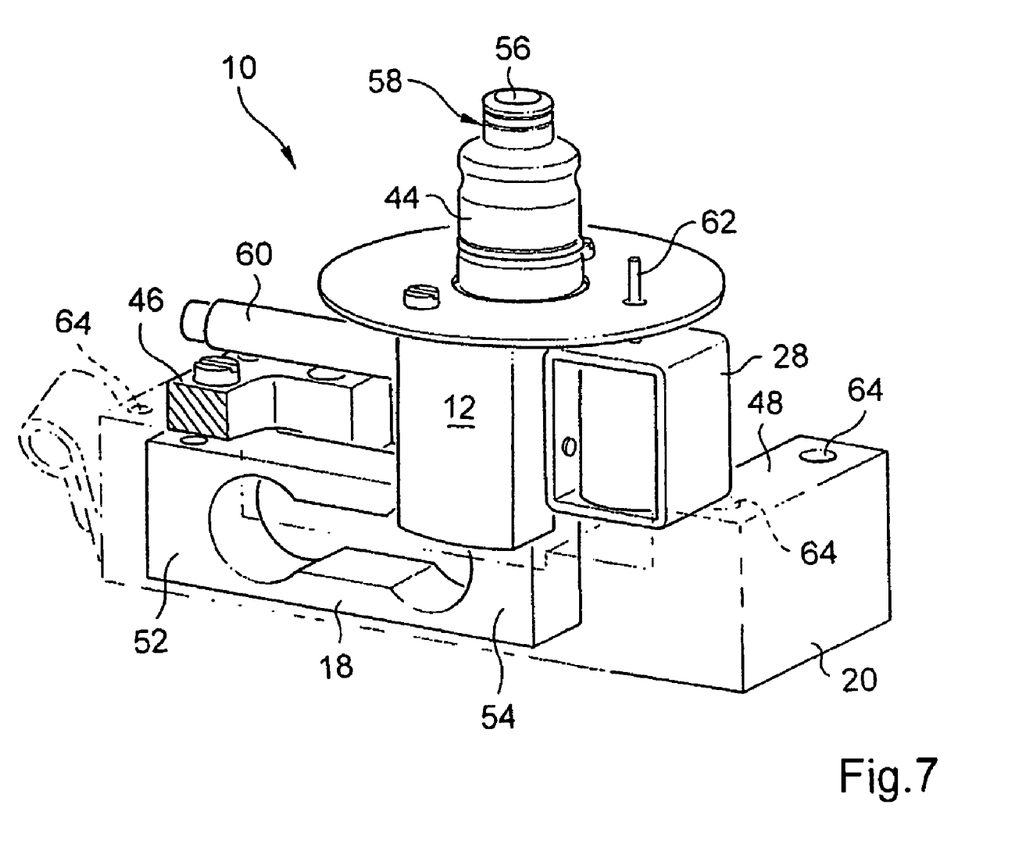
FIG. 7 is a diagrammatic opened up perspective view of details of the drainage device shown in FIG. 2.

FIG. 7 is a perspective view of the frame 20, the head support 12, and the weight sensor 18.

The frame 20 forms a cradle extending between a first end 46 and a second end 48 and having a central opening 50 that extends longitudinally between the first end 46 and the second end 48 and in which the weight sensor 18 is accommodated.

The latter sensor has a first end 52 entirely fastened to the first end of the frame 46 and extends longitudinally in the opening 50 as far as a second end 54.

The head support is mounted to bear on the second end 54 of the weight sensor 18 facing the frame 20.

Obviously, the head support 12 and the second end 54 of the weight sensor 18 are entirely unrestrained relative to the frame 20. Only the first end 52 of the weight sensor 18 is fastened to the frame 20.

As a result, the only loads exerted on the weight sensor 18 are the result of the weight of the head support 12, the head 14 and the filter unit. The weight exerted by these components on the second end 54 of the weight sensor 18 deforms it and a strain gauge, not shown, mounted on said weight sensor 18 delivers an electrical signal whose magnitude is a function of the weight exerted on said weight sensor.

The head support 12 includes an suction branch 56 having a first end discharging at the upper end 58 of the projecting vertical portion 44 and a second end discharging laterally of the head support 12 and adapted to be connected to a flexible portion of a tubular member 60.

FIG. 7 also shows the control device 28 entirely fastened to the head support 12 and consisting of a solenoid adapted to move in translation a punch 62 substantially parallel to said projecting vertical portion 44.

The frame 20 also has tapped holes 64 at each end for fixing the frame to the internal wall of the casing 34.

FIG. 3 shows the reception head 14, which is adapted to bear on the head support 12.

To this end, the reception head 14 has an axial opening 66 formed in its lower wall 68 and adapted to receive the projecting vertical portion 44 of the head support 12. The reception head 14 has a reception surface 70 onto which discharges an suction duct 72 communicating with the axial opening 66. The suction branch 56 is adapted to be connected, at the end 58 of the projecting vertical part 44, to the suction duct 72 of the reception head 14 when the latter is mounted on the head support 12.

The connection between the suction branch 56 and the suction duct 72 must be sealed to prevent leaks of water or air, and to this end the projecting vertical portion 44 and the axial opening 66 of the head are circular cylinders to enable insertion of seals 74.

The projecting vertical portion 44 has a shoulder 76 against which a corresponding shoulder 78 of the reception head 14 can bear. Thus the reception head 14 is adapted to be immobilized in translation.

The projecting vertical portion 44 has a groove 78 into which removable key means 80 mounted in said reception head 14 are adapted to be extended.

The key means 80 are described with reference to FIG. 6, which is a view in section taken along the line VI-VI of the reception head 14 shown in FIG. 3.

Figure 6:
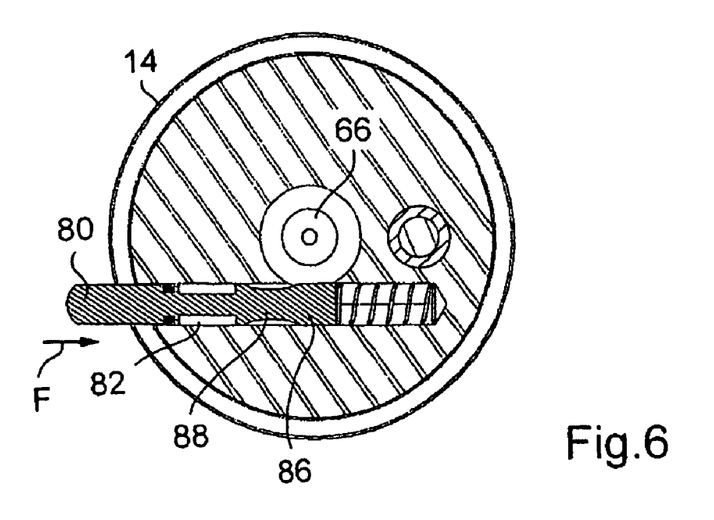
FIG. 6 is a view in section taken along the line VI-VI in FIG. 4.

FIG. 6 shows the axial opening 66 and the removable key means 80, which are mobile in translation in a lateral bore 82 in the reception head 14, and a portion 84 of which intersects the axial opening 66.

The removable key means 80 consist of a rod having a portion 86 with a section substantially equal to the section of the transverse bore 82 and a smaller section portion 88.

As shown in FIG. 6, the portion 86 of the removable means 80 intersects the axial opening 66 with the result that this portion is adapted to be engaged in the groove 78 of the projecting vertical portion 44 of the head support 12 and thus to connect together the projecting vertical portion 44 and the reception head 14. When the removable means 80 are actuated in the direction of the arrow F, the portion 88 is disposed facing the axial opening 66, but does not intersect said axial opening 66, with the result that it is totally unrestrained and the reception head 14 can be mounted on the head support 12 or removed therefrom.

Figure 4:
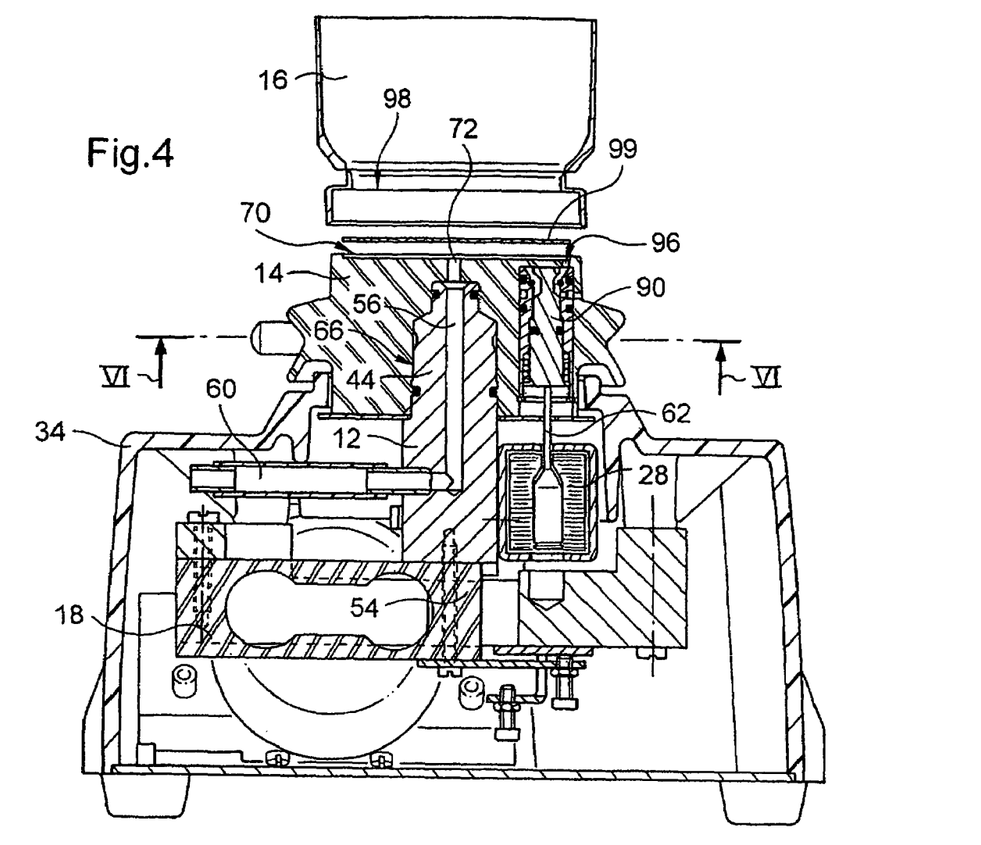
FIG. 4 is a diagrammatic view in vertical cross section taken along the line IV-IV in FIG. 3.

Refer next to FIG. 4, showing the drainage device according to the invention in vertical cross section.

This figure shows the casing 34 of the drainage device, the weight sensor 18, the head support 12 and its projecting vertical portion 44 engaged in the axial opening 66 in the reception head 14. It also shows the control device 28 whose punch 62 actuates a valve 90 accommodated in the reception head 14 and described in more detail with reference to FIG. 5.

Figure 5:
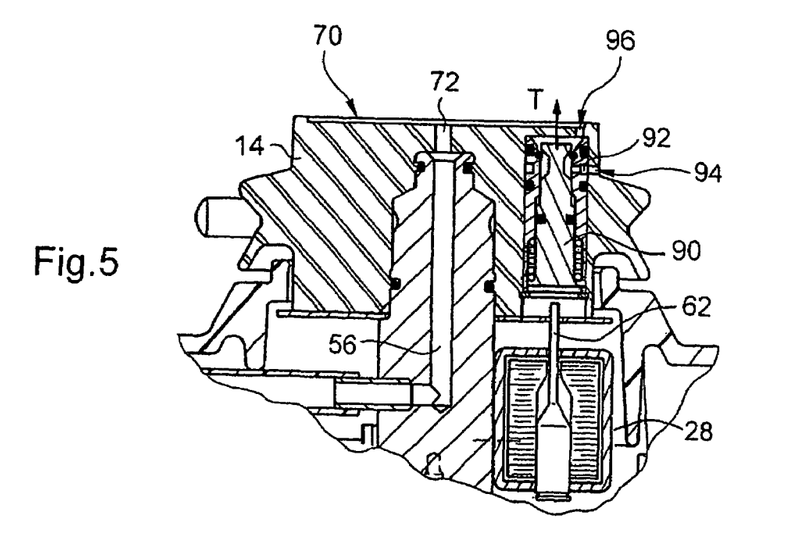
FIG. 5 is a diagrammatic view in section of a detail from FIG. 4.

FIG. 5 shows a reception head 14 mounted on the head support 12, part of which is shown. The control device 28 fastened to the head support 12 is inactive in this figure.

This figure shows the reception surface 70 of the reception head 14 and the suction duct 72 which discharges onto it.

The reception head 14 includes a passage 92, one end 94 of which discharges to the atmosphere on the exterior of the reception head 14, and the other end 96 of which discharges onto the reception surface 70. In this figure, the passage 92 is shut off by the valve 90. The latter valve moves in vertical translation as shown by the arrow T, to free the passage 92 and enable external air to flow from the end 94 towards the end 96 that discharges onto the reception surface 70.

By activating the control device 28, which consists of a solenoid, the punch 62, which is disposed on the axis of the selectively operable valve 90, is adapted to come to bear against the selectively operable valve 90 in order to free the passage 92, as shown in FIG. 4.

FIG. 4 also shows the filter unit 16, which includes a membrane 98 facing the reception surface to form a suction chamber 70. The membrane 98 is fastened to the filter unit 16 and is separated from the reception surface 70 by a sterile separator 99, consisting of a grid approximately 0.5 mm thick, to prevent it coming directly into contact with the suction surface. The sterile separator 99 extends throughout the suction chamber.

When the filter unit 16 is bearing directly on the reception head 14, which in turns bears on the support 12, this assembly is supported only by the second end 54 of the weight sensor 18. The weight sensor 18 is therefore able to supply a signal representative of the weight of a liquid substance contained in the filter unit 16 and of the variation in that weight.

A general flowchart of the operation of the drainage device according to the invention is described next with reference to FIG. 9.

First of all, in a first step, data is entered into the memory of the control unit 24 via the user interface 26. The data concerns, in particular, the operating mode to be used, the total volume of liquid substance to be filtered, the density of the liquid substance, and the type of filter unit mounted on the reception head 14.

As soon as this first weight is reached, the operator ceases to fill the filter unit 16 and, in a fourth step 106, the control unit starts the suction pump 22. As a result, the liquid substance contained in the filter unit 16 is aspirated through the membrane 98 and evacuated into the suction branch 56 via the suction duct 72.

Thus all of the liquid substance contained in the filter unit passes through the membrane 98, which retains the microorganisms that said liquid substance contains.

Clearly, when all of the liquid substance has been aspirated, the weight of the filter unit 16 is constant and the weight sensor 18 therefore delivers a stationary signal.

In a fifth step 108, the control unit stops the suction pump 22 as soon as the weight sensor 18 supplies this stationary signal.

Figure 9:
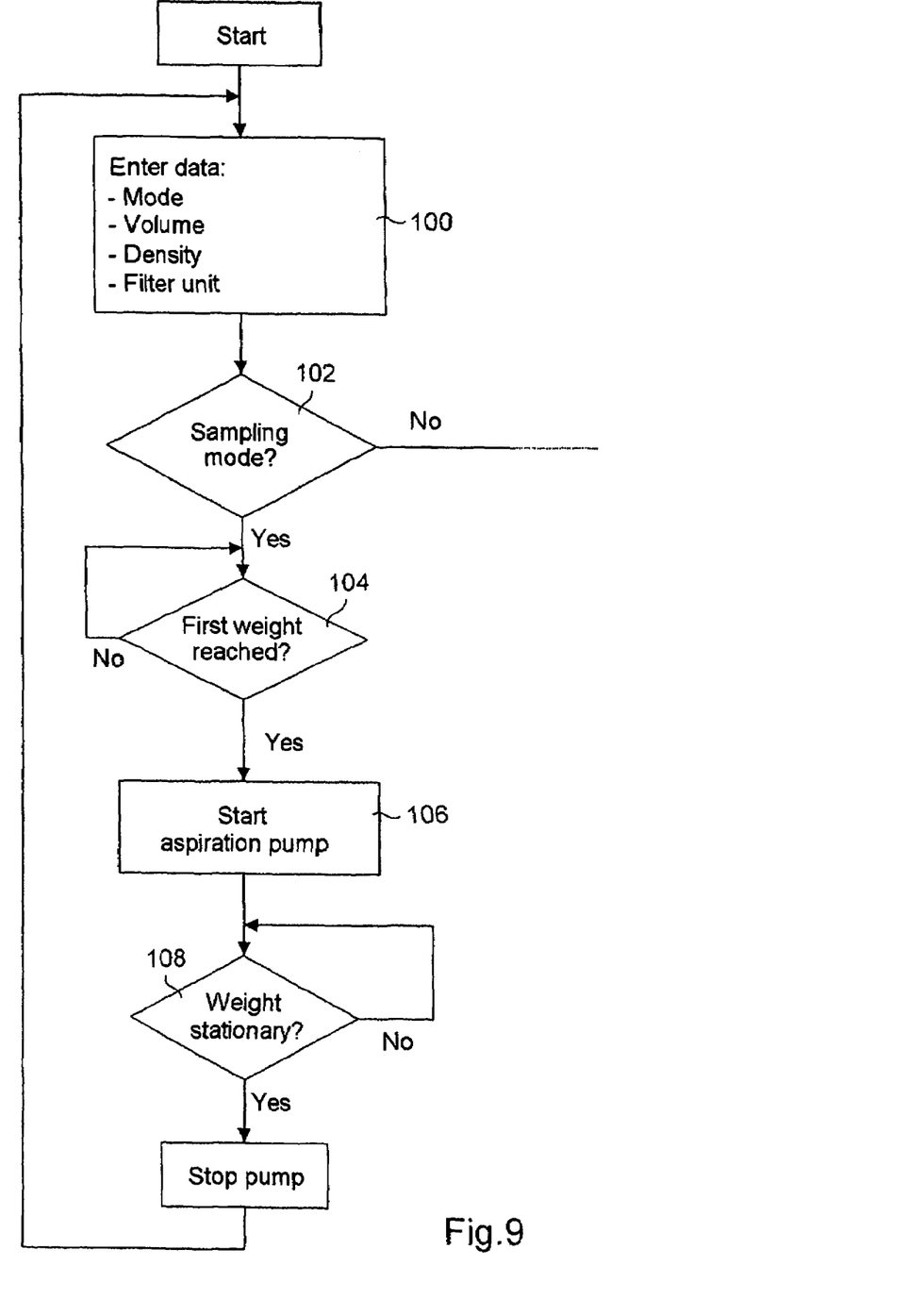
FIG. 9 is a general flowchart of the operation of the drainage device according to the invention.
Figure 10:
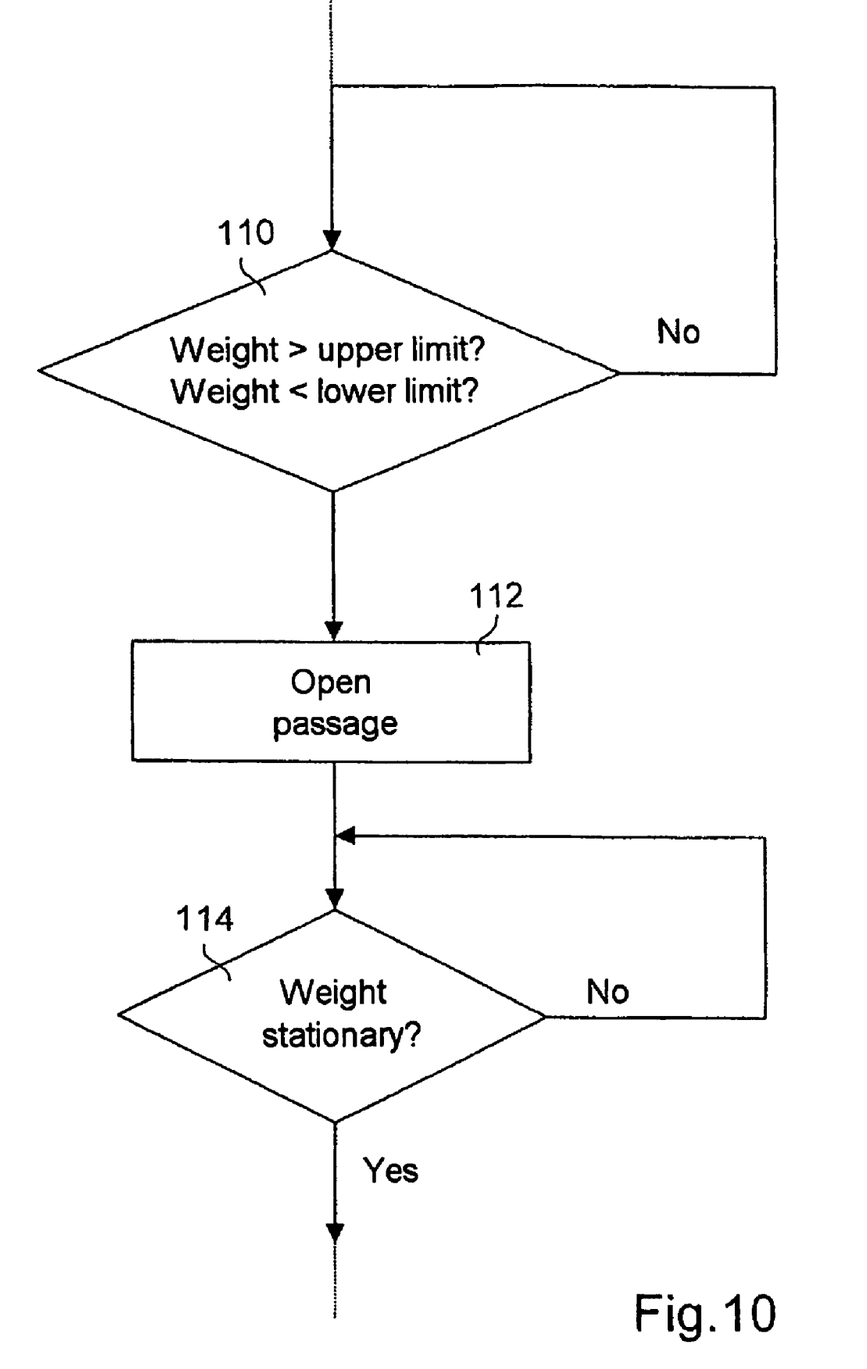
FIG. 10 shows a portion of the flowchart of a first function of the drainage device.

FIG. 10 shows a flowchart portion constituting steps of a first function complementary to the sequence of operations shown in the FIG. 9 flowchart.

This flowchart portion concerns a sequence of operations executed before data entry or after stopping the suction pump 22 when the liquid substance has been aspirated, to prevent the membrane 98 from bursting when the control unit 16 is mounted on or removed from the reception head 14.

When the filter unit 16 is forcibly nested over the reception head 14, a volume of air is trapped between the membrane 98 and the reception surface 70, which together form the suction chamber, and because the membrane 98 is only slightly permeable to air, the compression of this volume of air tends to compress the membrane and possibly burst it.

The converse phenomenon occurs when the filter unit 16 is removed from the reception head 14, a reduced pressure being created between the membrane 98 and the reception surface 70, with the risk of rupturing the membrane 98.

In a first step 110 shown in FIG. 10, the control unit 24 verifies that the weight sensor 18 is supplying a signal representative of an upper limit weight, greater than the weight of the liquid substance likely to be contained in the filter unit, and which is representative of the force exerted on the reception head 14 when the filter unit 16 is nested.

In a second step 112, when the weight sensor 18 supplies a signal representative of the upper limit weight, the control unit 24 actuates the solenoid 28 which causes the valve 90 to move and free the passage 92. As a result, the air trapped between the membrane 98 and the reception surface 70 escapes via the first end 94 of the passage 92 and is not compressed against the membrane 98.

Then, in a third step 114, the control unit 24 continues the sequence when the weight sensor 18 supplies a stationary signal representative of a constant weight.

In the same way, when the weight sensor 18 supplies a signal representative of a negative weight, which might correspond to a step of removing the filter unit 16 from the head support 14, the control unit 24 opens the passage 92 to prevent the membrane from bursting.

Figure 11:
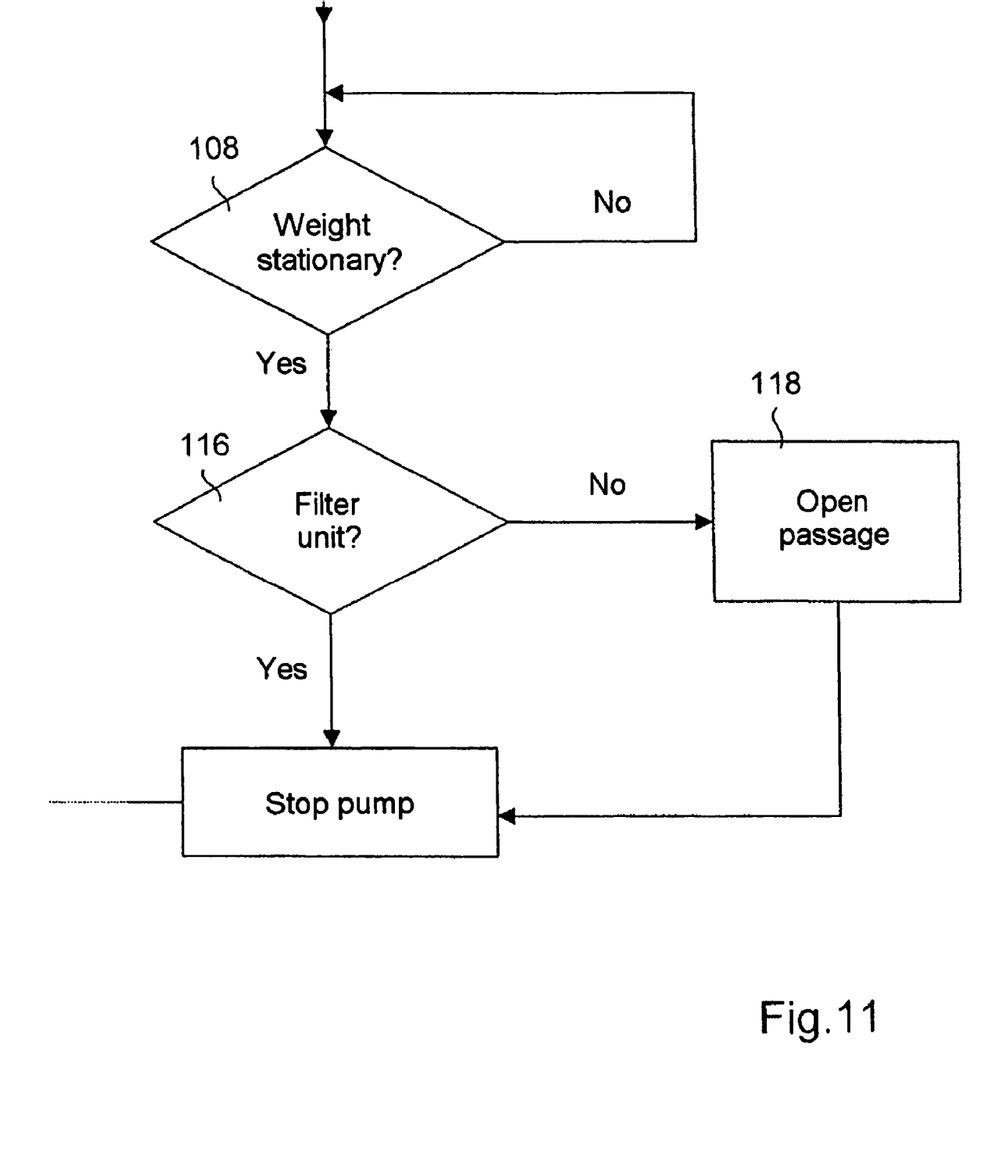
FIG. 11 shows a portion of the flowchart of a second function of the drainage device.

FIG. 11 shows complementary steps for drying the member 98 after the liquid substance has been filtered, this sequence being implemented for certain types of filter unit.

FIG. 11 shows the step 108 shown in FIG. 9 in which the flow of the liquid substance is commanded. As soon as it has all flowed, if the sequence authorizes it and by virtue of the filter unit type entered with the input data, a step 116 opens the passage 92 in a step 118. The suction pump 22 is then stopped in a final step.

As a result, as soon as the suction pump 22 is operating, the membrane 98 being relatively impermeable, air aspirated from the outside flows through the passage, between the membrane 98 and the reception surface 70, and then via the suction duct 72. This dries the membrane 98, which can be placed directly on a culture substrate.

Figure 12:
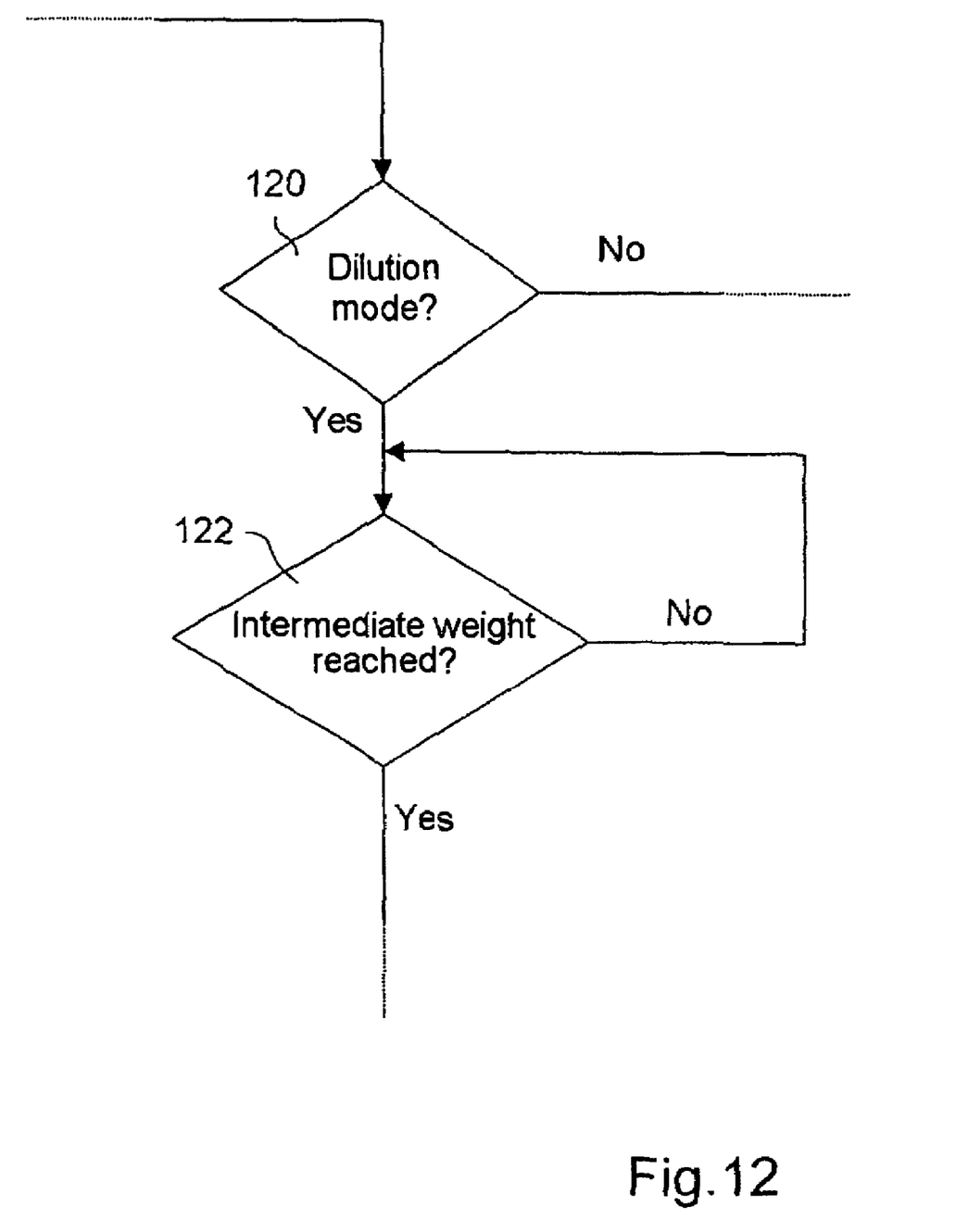
FIG. 12 shows a portion of the flowchart of a third function of the drainage device according to the invention.

FIG. 12 shows complementary steps of a different embodiment of the invention for filtering a mixture of two liquid substances.

FIG. 9 shows a step 102 for selecting the operating mode. If the mode chosen is not the sampling mode represented in FIG. 9, but instead a dilution mode, for example, the sequence includes complementary steps 120 and 122 shown in FIG. 12.

Choosing the dilution mode necessitates first entering the data corresponding to the two liquid substances to be mixed, one after the other. This data relates in particular to volume and density.

When the first liquid substance is poured into the filter unit 16, the control unit 24, which displays the volume added on the display screen, triggers an audible alarm indicating that a volume of the first liquid substance has been introduced that corresponds to an intermediate weight measured by the weight sensor 18.

The next step then corresponds to the third step 104 shown in FIG. 9, in which starting of the suction pump is authorized only if the volume of the second liquid substance has been introduced.

It is still necessary to enter data into the memory of the control unit 24 before filling the filter unit and filtering the liquid substance.

The data includes in particular information concerning the filter process itself and information on the type of filter unit liable to be fitted to the reception head 14.

One essential feature of the invention is that the mechanical support comprises a removable reception head 14 that can be locked to a head support 12.

Examples of reception heads for filtering a liquid substance or liquid substances with different types of filter unit are described with reference to FIG. 8.

Figure 8:
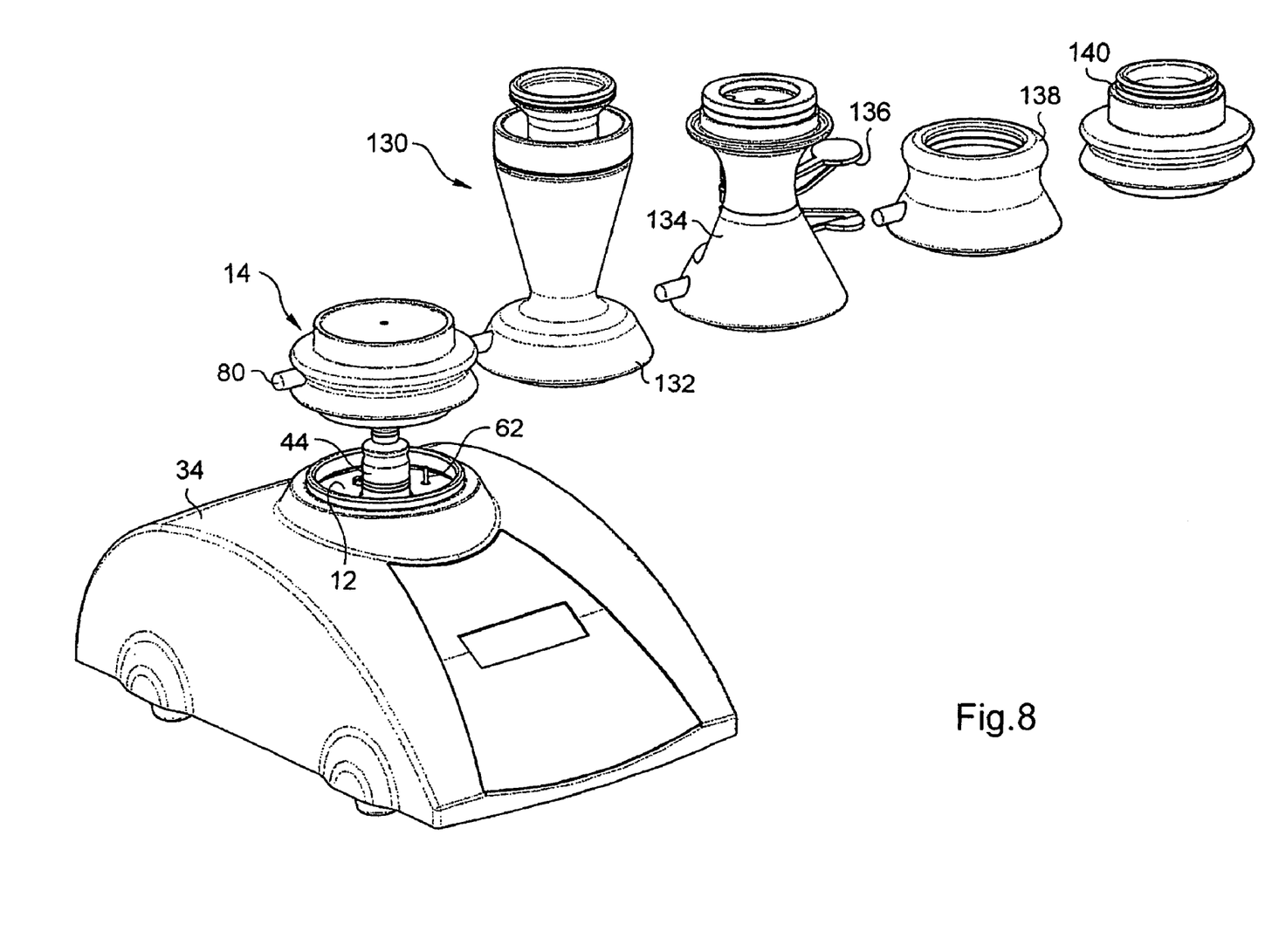
FIG. 8 is a diagrammatic perspective view showing different embodiments of the drainage device according to the invention.

FIG. 8 shows the drainage device according to the invention facing the head support 12 on which the reception head 14 is disposed.

FIG. 8 also shows a second type of reception head 130 including a special clipping system for the filter unit.

The second type of reception head 130 has at the bottom lockable connecting means identical to the reception head 14 so that it can be mounted in the same way on the head support 12.

This second type of reception head has no selectively operable valve and is heavier than the reception head 14.

Thus it is clear that the input data has to be modified and especially that concerning the mode of operation and the type of filter unit. As a result, the drainage device according to the invention can take account of the initial weight differences and the filter process, which includes no step of drying the membrane.

A third type of reception head 134, which also has at the bottom lockable connecting means identical to the previous means, is used to filter a liquid substance via a membrane deposited on a sintered material. To this end it has a handle 136 for removing the sintered material.

This third type of reception head also necessitates the entry into the control unit of data differing from the previous data.

Two other types of reception head 138 and 140 are also adapted to be removably mounted on the head support 12, the first including a selectively operable valve adapted to be activated by the punch 62 and the second having no such valve.

Obviously, these other two reception heads 138, 140 necessitate the entry of specific data before they can be used.

The types of reception head previously described can be sterilized by any means and independently of the device.

The present invention is in no way limited to the embodiments described and shown, which the person skilled in the art will know how to modify within the spirit of the invention.

The invention claimed is:

1. A drainage device for a filter unit for microbiological testing of liquids, wherein said drainage device comprises:
   (a) a mechanical support comprising a reception head for receiving a filter unit including a membrane;
   (b) a suction pump connected to said mechanical support to aspirate a liquid substance contained in said filter unit;
   (c) a weight sensor on which said mechanical support is mounted and which is adapted to deliver a signal representative of the weight exerted by said mechanical support on said weight sensor;
   (d) a user interface for entering data relating to the drainage of said filter unit and/or to said liquid substance; and
   (e) a control unit connected to said suction pump, the weight sensor and said user interface, said control unit being adapted to determine, from said data, at least a first weight corresponding to a first representative signal; and in that, when said weight sensor supplies a signal corresponding to said first signal, said control unit starts operation of said suction pump so as to aspirate said liquid substance contained in said filter unit.

2. The drainage device according to claim 1 wherein said reception head comprises a reception surface opposite which said membrane can be disposed and onto which a suction duct discharges, and in that said reception head includes a passage, one end of which discharges externally of said reception surface and the other end of which discharges onto said reception surface, said reception head comprising a selectively operable valve mobile between a first position in which it shuts off said passage and a second position in which it frees said passage.

3. The drainage device according to claim 1 wherein said reception head comprises a selectively operable valve mobile between a first position in which it shuts off said passage and a second position in which it frees said passage, said control unit commands movement of said selectively operable valve into said second position and starts the operation of said suction pump when said weight sensor supplies a stationary signal representative of a constant weight exerted on said weight sensor by said mechanical support after said liquid substance has been aspirated.

4. The drainage device according to claim 1 wherein said reception head comprises a selectively operable valve mobile between a first position in which it shuts off said passage and a second position in which it frees said passage, said control unit commands movement of said selectively operable valve into said second position when said weight sensor supplies signals respectively representative of an upper limit weight when said filter unit, is placed on said reception head and a lower limit weight when said filter unit is removed from said reception head.

5. The drainage device according to claim 1 further comprising a frame, wherein said weight sensor extends substantially horizontally between a first end fastened to said frame and a second end that is free with respect to said frame, and said mechanical support rests on said second end of said weight sensor.

6. The drainage device according to claim 5 further comprising an armature covered with a casing, bearing on a chassis, wherein said frame is suspended from said armature in the space between said chassis and said armature, and an opening in the casing facing said head support is adapted for mounting and demounting a reception head.

7. The drainage device according to claim 1 wherein said mechanical support is connected to said suction pump by a tubular member having at least one flexible portion that extends from said mechanical support substantially perpendicularly to the direction of operation of said weight sensor.

8. The drainage device according to claim 1 further comprising a reception head support entirely fastened to said weight sensor and wherein said reception head is removably fastened to said head support with lockable connecting means.

9. The drainage device according to claim 8 wherein said reception head support has a circular cylindrical projecting vertical portion adapted to cooperate with an opening formed in the portion opposite a reception surface of said reception head and said reception head and said projecting vertical portion are fastened together by keying means to form said lockable connecting means.

10. The drainage device according to claim 8 wherein said reception head has a transverse bore adapted to cooperate with a groove formed around said vertical portion and said transverse bore is adapted to receive removable key means.

11. The drainage device according to claim 8 wherein said head support has an suction branch, one end of which is adapted to be connected to a suction duct of said reception head and the other end of which is adapted to be connected to said suction pump.

12. The drainage device according to claim 8 wherein said head support includes a control device adapted to cooperate with a selectively operable valve to move it into said first position or into said second position.

13. The drainage device according to claim 12 wherein said control device includes a solenoid whose core is adapted to drive said selectively operable valve.

* * * * *